United States Patent [19]

Kramer

[11] 4,371,786

[45] Feb. 1, 1983

[54] METHOD AND APPARATUS FOR DETECTING BUBBLES IN A LIQUID

[75] Inventor: Donald L. Kramer, Indian Harbor Springs, Fla.

[73] Assignee: Miles Laboratories, Inc., Elkhart, Ind.

[21] Appl. No.: 201,736

[22] Filed: Oct. 29, 1980

[51] Int. Cl.³ .............................................. A61M 5/16
[52] U.S. Cl. .................................. 250/343; 250/573; 356/410
[58] Field of Search ....................... 250/343, 345, 573; 356/410

[56] References Cited

U.S. PATENT DOCUMENTS

| | | | |
|---|---|---|---|
| 3,909,136 | 9/1975 | Thomas | 356/410 |
| 3,910,701 | 10/1975 | Henderson et al. | 356/73 X |
| 4,312,341 | 1/1982 | Zissimopoulos et al. | 356/410 X |

*Primary Examiner*—David C. Nelms
*Assistant Examiner*—Darwin R. Hostetter
*Attorney, Agent, or Firm*—Joseph C. Schwalbach

[57] ABSTRACT

A method and apparatus for sensing the presence of bubbles in a liquid wherein radiation is directed through said liquid toward a radiation responsive sensor and the differential between the response of the sensor when a bubble is not present in the radiation path and the response thereof when a bubble is present in the radiation path is markedly increased by limitation of the radiation which can reach said sensor to wavelengths strongly absorbed by said liquid.

28 Claims, 2 Drawing Figures

METHOD AND APPARATUS FOR DETECTING BUBBLES IN A LIQUID

BACKGROUND OF THE INVENTION

This invention relates to sensing the presence of bubbles in a liquid, and a particular application thereof is the detection of air bubbles in serum or blood during infusion thereof into a patient. In such procedures it is important to insure that gas or air be prevented from being infused with the liquid, since air emboli can be extremely dangerous in a patient, particularly if the patient is very sick or is a premature or sick newborn.

Various instruments have been developed for preventing air bubbles from being infused into a patient along with a liquid, typical of which are those disclosed is U.S. Pat. Nos. 2,835,252, 3,812,842, 3,935,876 and 4,114,144. Such instruments typically provide an alarm and/or shut off mechanism which is activated when air bubbles are sensed in the infusion liquid being monitored. They may also provide readout means indicating the volume infused up to the cut-off point. Such prior instrumentation commonly suffers from unreliable operation because of low signal level, electronic drift, and/or difficult mechanical alignment.

SUMMARY OF THE INVENTION

The present invention avoids problems inherent in certain of the prior instruments primarily by virtue of the markedly increased signal response generated by a sensor when the presence of a bubble in the liquid being monitored is sensed thereby.

More particularly, the invention exploits the radiation absorptivity characteristics of the liquid being monitored to produce a markedly increased differential between the output of the sensor when a bubble is not sensed and the output thereof when a bubble is sensed, such increased differential being effected by directing radiation through the liquid and toward the sensor, and by limiting the radiation which can reach the sensor to wavelengths which are strongly absorbed by the liquid.

The preferred embodiment of the invention is particularly adapted for sensing the presence of air bubbles in an aqueous liquid such as serum or blood. Markedly increased signal response is produced as a result of limitation of the radiation which can reach the sensor to wavelengths above one micrometer, and preferably about 1.92 micrometers, water being strongly absorptive of radiation of such wavelengths.

Other objects, features and advantages of the invention will become apparent as the description proceeds, reference being had to the accompanying drawing.

DESCRIPTION OF THE PREFERRED EMBODIMENT

Figure 1:
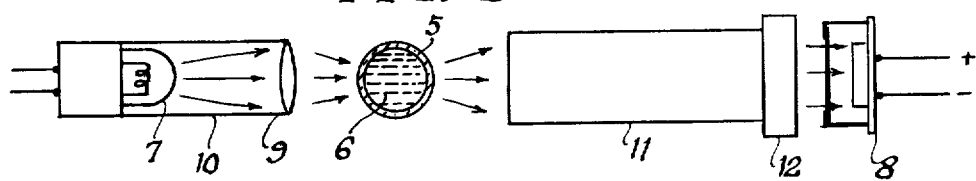
FIG. 1 is a diagrammatic illustration of the preferred form of the invention.

FIG. 1 diagrammatically illustrates apparatus for detecting bubbles in a liquid in accordance with the present invention. In FIG. 1 the numeral 5 indicates a tube shown in transverse cross-section, which tube is formed of radiation-transmissive material such as transparent glass or plastic. Tube 5 may form part of a system (not shown) for infusion of a liquid such as blood or serum into a patient and is adapted to contain the liquid 6 to be monitored for bubble content as it flows from a source to the patient.

Means is provided for directing radiation from a radiation source 7 through the liquid 6 in tube 5 and toward a radiation-responsive sensor 8. The radiation source 7 preferably takes the form of an incandescent lamp connected to a suitable source of electric power (not shown) and operated at a low color temperature, i.e., at about 1500° K. As shown by the arrows, radiation from lamp 7 is focused on the bore of tube 5 by a lens 9 which may be carried by a tube 10.

Wide aperture radiation collection means 11, which may take the form of a fibre optic cyclinder or other suitable wide aperture optical system, is positioned on the opposite side of tube 5 from lamp 7 in alignment with the tube 10. Collection means 11 collects radiation from source 7 which has passed through the tube 5 and transmits such radiation longitudinally thereof toward the sensor 8.

Means is provided for limiting the radiation from the source 7 which can reach the sensor 8 to a predetermined wavelength which is strongly absorbed by the liquid 6. In the illustrated embodiment such means takes the form of a filter 12 which is interposed between the collection means 11 and the sensor 8.

The apparatus of the present invention may form a part of a system (not shown) having an electrical control circuit to which the sensor 8 is connected. Such system may have means responsive to an output signal from sensor 8 for cutting off the flow through tube 5 and for indicating the amount of liquid infused up to the cut-off point and/or for sounding an alarm when a bubble is present in the tube 5 and intersects the radiation path therethrough.

Figure 2:
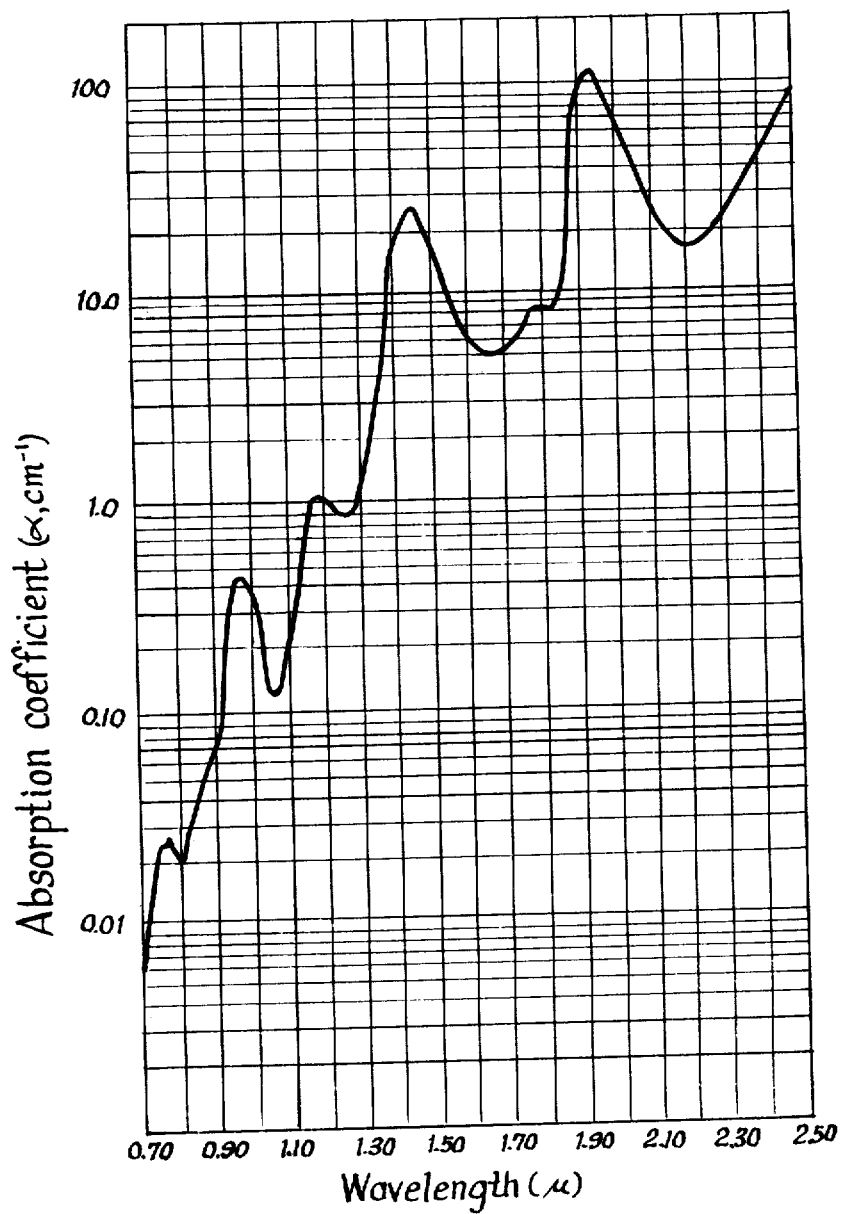
FIG. 2 is a graphic logarithmic illustration of the absorption coefficient of water with respect to radiation having wavelengths of from 0.70 to 2.50 micrometers.

The inventive concept underlying the method and apparatus disclosed herein will be best understood with reference to FIG. 2 of the drawing. In FIG. 2 the absorption coefficient of water ($\alpha$, $CM^{-1}$) with respect to radiation of wavelengths between 0.70 and 2.50 micrometers ($\mu$) is plotted on a logarithmic scale. It will be observed that the curve developed is characterized by a series of peaks of dramatically increasing absorptivity for radiation of linearly increasing wavelengths. The following table sets forth the approximate wavelength/absorptivity relationships in the areas of the aforenoted peaks.

| Wavelength ($\mu$) | Absorption Coefficient ($\alpha$, $CM^{-1}$) |
|---|---|
| 0.77 | 0.027 |
| 0.98 | 0.45 |
| 1.19 | 1.00 |
| 1.45 | 25.00 |
| 1.92 | 106.00 |

Prior art photodetector instruments in general utilize radiation of visible wavelengths and into the infra red range up to about 0.98$\mu$. It will be observed that the absorption coefficient of water for radiation of a wavelength of 0.98$\mu$ is 0.45$\alpha$, $CM^{-1}$. However, the absorption coefficient of water for radiation of longer wavelengths of 1.19, 1.45 and 1.92$\mu$ is respectively 2.22, 55.55 and 235.55 times the 0.45α, CM$^{-1}$ absorption coefficient of water for radiation of 0.98μ wavelength.

The present invention exploits the illustrated absorptivity characteristics to provide a dramatically increased differential between the response of the sensor 8 when a bubble is not present in the radiation path and the response thereof when a bubble is present in the radiation path. This is accomplished by the use of the filter 12 to limit the radiation which can reach the sensor 8 to that which is strongly absorbed by the liquid 6, i.e. radiation having a wavelength greater than one micrometer. The dramatically increased differential mentioned is reflected in a corresponding marked increase in signal response to sensor 8 when a bubble is present in the radiation path.

While the invention will produce substantially increased signal response by sensor 8 if filter 12 limits the radiation which can reach the sensor to any wavelength above 1μ, including the peaks at 1.19, 1.45 and 1.92μ, it is presently preferred to use as filter 12 a narrow bandpass interference filter which limits such radiation to that having a wavelength of 1.92μ, i.e. the wavelength at which the strongest absorption occurs on FIG. 2. Wavelengths longer than 2.5μ can advantageously be used, but they are not preferred because of the requirement for special circuitry or other provision for physically cooling the sensor 8 when such wavelengths are used.

The sensor 8 selected preferably has peak responsivity at or near the wavelength of the radiation to be sensed thereby. More particularly, when a filter 12 is used which limits the radiation which can reach the sensor 8 to a wavelength of 1.92μ, the preferred sensor 8 for use therewith is a lead sulfide thermal detector which has a response range of from about 1.2μ to about 2.5μ and a peak responsivity at about 2.0μ.

Referring again to FIG. 1, the operation of the illustrated apparatus will now be described. With an aqueous liquid 6 to be monitored, such as serum or blood, flowing through the tube 5, radiation from the lamp 7 is focused on said liquid by the lens 9 and is partially absorbed by said liquid. The portion of such radiation which is not absorbed enters the radiation collector 11 and is transmitted to the filter 12 which permits only that portion of such radiation having a wavelength of 1.92μ to reach the sensor 8. As shown on FIG. 2, water absorbs such radiation very strongly, hence little such radiation reaches the sensor 8 and the output thereof is substantially zero.

If an air bubble passes through the tube 5, displacing the liquid 6 in the path of radiation from lamp 7 to sensor 8, only a negligible amount of such radiation is absorbed by such bubble. Such radiation passes through the tube 5 substantially undiminished, is collected by collector 11 and transmitted thereby to the filter 12. Since filter 12 permits only that portion of such radiation having a wavelength of 1.92μ to reach the sensor 8, the difference in absorptivity of radiation of that wavelength by air as compared to absorptivity thereof by water results in a very large differential in the signal response of sensor 8 as compared to that produced when a 0.98μ filter commonly used in prior art photodetectors is used.

The increased differential in signal response produced by the present invention can be illustrated by the following procedure. The sensor 8 of the apparatus illustrated in FIG. 1 is connected to the input of an amplifier (not shown) whose output is adjustable and is read in millivolts. The tube 5 is removed from the radiation path so that the sensor 8 is exposed to the maximum amount of radiation from lamp 7. The output of the amplifier is then adjusted arbitrarily to 100 millivolts, after which the tube 5 is repositioned in the radiation path as shown in FIG. 1. Because of reflection, refraction and/or absorption of radiation resulting from the repositioning of the tube 5, the radiation reaching the sensor 8 is reduced, and the sensor output is correspondingly reduced, so that the output of the amplifier drops to 90 millivolts. Since no liquid is present in the tube 5, this represents the response of the sensor 8 when an air bubble is present in the radiation path. Moreover, the output of the sensor is likely to be substantially the same in this situation if the filter 12 is one which limits the radiation which can reach the sensor 8 to 0.98μ wavelength or is one which limits such radiation to 1.92μ wavelength.

The tube 5 is then filled with water, and for the filter 12, a filter is used which limits the radiation which can reach the sensor 8 to that having a wavelength of 0.98μ. Since the absorptivity of water is only about 0.45α, CM$^{-1}$ at this wavelength (see FIG. 2), i.e. it is very low, the amount of radiation of 0.98μ wavelength reaching the sensor 8 is only very slightly reduced by water absorption so that the output of the amplifier drops to 88 millivolts.

A 1.92μ filter is then used as the filter 12 instead of the 0.98μ filter. Since the absorptivity of water at this wavelength is 106. α, CM$^{-1}$ (see FIG. 2), i.e. very strong, substantially all of the radiation of 1.92μ wavelength is absorbed by the water so that the output of the sensor 8 and of the amplifier drop to substantially zero.

From the foregoing illustration it is apparent that by limiting the radiation which can reach the sensor to that which is strongly absorbed by the liquid being monitored, the signal response of a photodetector to the presence of a bubble in the liquid can be dramatically increased. More specifically, it will be observed in the foregoing illustration that when a 0.98μ filter is used, the amplifier output when a bubble is present is only two millivolts higher than when liquid is present in the radiation path. In marked contrast to the minimal response produced when a 0.98μ filter is used, when a 1.92μ filter is used, the amplifier output when a bubble is present is 90 millivolts higher than when liquid is present in the radiation path. The signal response resulting from the practice of the present invention is thus about 45 times greater than that which is attained in prior art bubble sensing apparatus.

Having described one embodiment of the invention, it will be understood that various changes and modifications may be made in the disclosed embodiment without departing from the spirit of the invention, and all of such changes are contemplated as may come within the scope of the appended claims.

What is claimed as the invention is:

1. In the method of detecting the presence of bubbles in a liquid by sensing the effect of absorption by the liquid of radiation directed therethrough, the improvement which markedly increases the differential between the amount of radiation transmitted along a radiation path through the liquid when a bubble is not present in the radiation path and a greater amount of radiation transmitted through a bubble in the liquid present in the radiation path, comprising directing along said radiation path radiation having wavelength greater than 1.0 micrometer, and detecting the radiation having a wavelength greater than 1.0 micrometer which has traversed said radiation path.

2. The improved method of claim 1 wherein the liquid is an aqueous liquid.

3. An improved method of claim 1 wherein the liquid is blood.

4. The improved method of claim 1 wherein the radiation directed along said radiation path is filtered to limit the detected radiation to that having a wavelength greater than 1.0 micrometer.

5. The improved method of claim 1 wherein at least some of the radiation directed along the radiation path has a wavelength of between about 1.0 and 2.5 micrometers, and the radiation detected is that having a wavelength of between about 1.0 and 2.5 micrometers.

6. The improved method of claim 1 wherein at least some of the radiation directed along the radiation path has a wavelength of between about 1.4 and 2.5 micrometers, and the radiation detected is that having a wavelength of between about 1.4 and 2.5 micrometers.

7. The improved method of claim 1 wherein at least some of the radiation directed along the radiation path has a wavelength of about 1.45 micrometers, and the radiation detected is that having a wavelength of about 1.45 micrometers.

8. The improved method of claim 1 wherein at least some of the radiation directed along the radiation path has a wavelength of about 1.92 micrometers, and the radiation detected is that having a wavelength of about 1.92 micrometers.

9. The improved method of claim 1 wherein the radiation is supplied by a lamp operated at a temperature of the order of 1500° K.

10. The improved method of claim 1 wherein the liquid is aqueous, the radiation is supplied by a lamp operated at a temperature of the order of 1500° K. the output of which includes radiation having a wavelength of between about 1.0 and 2.5 micrometers, and the radiation detected is that having a wavelength of between about 1.0 and 2.5 micrometers.

11. The improved method of claim 1 wherein the liquid is aqueous, the radiation is supplied by a lamp operated at a temperature of the order of 1500° K. the output of which includes radiation having a wavelength of about 1.92 micrometers, and the radiation detected is that having a wavelength of about 1.92 micrometers.

12. In apparatus for detecting the presence of bubbles in a liquid by sensing the effect of absorption by the liquid of radiation directed from a source thereof along a radiation path through the liquid and toward a radiation-responsive sensor, the improvement which markedly increases the differential between the signal response of the sensor when a bubble is not present in the radiation path and the higher signal response thereof when a bubble in the liquid is present in said path, wherein at least some of the radiation directed from the source along the radiation path has a wavelength greater than 1.0 micrometer, and the sensor is responsive to radiation having a wavelength greater than 1.0 micrometer.

13. The improved apparatus of claim 12 wherein the radiation source is a lamp operated at a temperature of the order of 1500° K.

14. The improved apparatus of claim 2 wherein at least some of the radiation directed from the source thereof along the radiation path has a wavelength of between about 1.4 and about 2.5 micrometers, and the sensor is responsive to radiation having a wavelength of between about 1.4 and 2.5 micrometers.

15. The improved apparatus of claim 12 wherein at least some of the radiation directed from the source thereof along the radiation path has a wavelength of about 1.45 micrometers, and the sensor is responsive to radiation having a wavelength of about 1.45 micrometers.

16. The improved apparatus of claim 12 wherein at least some of the radiation directed from the source thereof along the radiation path has a wavelength of about 1.92 micrometers, and the sensor is responsive to radiation having a wavelength of about 1.92 micrometers.

17. The improved apparatus of claim 2 having filter means in the radiation path for limiting to wavelengths greater than 1.0 micrometer the radiation from the source which can reach the sensor.

18. The improved apparatus of claim 12 having filter means in the radiation path for limiting to wavelengths between about 1.4 and about 2.5 micrometers the radiation from the source which can reach the sensor.

19. The improved apparatus of claim 12 having filter means in the radiation path for limiting to a wavelength of about 1.45 micrometers the radiation from the source which can reach the sensor.

20. The improved apparatus of claim 12 having filter means in the radiation path for limiting to a wavelength of about 1.92 micrometers the radiation from the source which can reach the sensor.

21. The improved apparatus of claim 12 having filter means in the radiation path for limiting to wavelengths greater than 1.0 micrometer the radiation from the source which can reach the sensor, said sensor and filter means being substantially matched such that the sensor has peak responsivity at substantially the wavelength of radiation from said source permitted by the filter means to reach said sensor.

22. The improved apparatus of claim 12 having filter means in the radiation path for limiting to wavelengths of about 1.4 to about 2.5 micrometers the radiation which can reach the sensor, and said sensor is responsive to radiation having a wavelength of from about 1.2 to about 2.5 micrometers.

23. The improved apparatus of claim 12 having a narrow bandpass interference filter in the radiation path for limiting to wavelengths of about 1.92 the radiation which can reach the sensor, and said sensor is a lead sulfide thermal detector responsive to radiation of a wavelength of from about 1.2 to about 2.5 micrometers and having a peak responsivity to radiation of a wavelength of about 2.0 micrometers.

24. The improved apparatus of claim 12 having filter means in the radiation path between the liquid and the sensor for limiting to wavelengths greater than 1.0 micrometer the radiation which can reach the sensor.

25. The improved apparatus of claim 12 wherein the liquid is contained in a radiation transmissive tube, there is means for focusing the radiation from the source toward the bore of the tube, and there is radiation collection means for collecting radiation from the source which has passed through the tube bore and for directing such radiation toward the sensor.

26. The improved apparatus of claim 12 wherein the liquid is contained in a radiation transmissive tube, there is wide aperature radiation collection means for collecting radiation from the source which has passed through the tube bore and for directing such radiation toward the sensor, and positioned between the collection means and the sensor is filter means for limiting to wavelengths greater than 1.0 micrometer the radiation which can reach the sensor.

27. The improved apparatus of claim 12 wherein the liquid is contained in a radiation transmissive tube, there is wide aperture fiber optic radiation collection means for collecting radiation from the source which has passed through the tube bore and for directing such radiation toward the sensor, and positioned between the collection means and the sensor is filter means for limiting to wavelengths greater than 1.0 micrometer the radiation which can reach the sensor.

28. The improved apparatus of claim 12 wherein the liquid is contained in a radiation transmissive tube; the radiation source is a lamp operated at a temperature of the order of 1500° K.; there is means for focusing the radiation from the lamp toward the bore of the tube; there is wide aperature radiation collection means for collecting radiation from the source which has passed through the tube bore and for directing such radiation toward the sensor; there is positioned between the collection means and the sensor a narrow bandpass interference filter which limits radiation which can reach the sensor to that having a wavelength of about 1.92 micrometers; and the sensor is a lead sulfide thermal detector responsive to radiation of a wavelength of from about 1.2 to about 2.5 micrometers and having a peak responsivity to wavelengths of about 2.0 micrometers.

* * * * *